United States Patent
Cole et al.

(10) Patent No.: US 7,544,701 B2
(45) Date of Patent: Jun. 9, 2009

(54) SULFONYLDIHYDROBENZIMIDAZOLONE COMPOUNDS AS 5-HYDROXYTRYPTAMINE-6 LIGANDS

(75) Inventors: Derek Cecil Cole, New City, NY (US); Ronald Charles Bernotas, Royersford, PA (US)

(73) Assignee: Wyeth, Madison, NJ (US)

(*) Notice: Subject to any disclaimer, the term of this patent is extended or adjusted under 35 U.S.C. 154(b) by 486 days.

(21) Appl. No.: 10/897,153

(22) Filed: Jul. 22, 2004

(65) Prior Publication Data

US 2005/0020575 A1 Jan. 27, 2005

Related U.S. Application Data

(60) Provisional application No. 60/489,417, filed on Jul. 23, 2003.

(51) Int. Cl.
A61K 31/454 (2006.01)
C07D 261/20 (2006.01)

(52) U.S. Cl. .................. 514/322; 546/193; 546/198; 514/318

(58) Field of Classification Search .................. 514/318, 514/322; 546/193, 198
See application file for complete search history.

(56) References Cited

U.S. PATENT DOCUMENTS

| 5,288,749 A | 2/1994 | Meyer et al. |
|---|---|---|
| 5,585,394 A | 12/1996 | Di Malta et al. |
| 6,686,374 B1 | 2/2004 | Edwards et al. |
| 6,699,880 B1 | 3/2004 | Yamakawa et al. |
| 6,770,642 B2 | 8/2004 | Cole et al. |

FOREIGN PATENT DOCUMENTS

| EP | 1994-4017316 | * | 7/1994 |
|---|---|---|---|
| EP | 0778277 A1 | | 6/1997 |
| JP | 2001058991 A | * | 3/2001 |
| WO | 0127104 | * | 4/2001 |

OTHER PUBLICATIONS

Dorwald F. A. Side Reactions in Organic Synthesis, 2005, Wiley: VCH, Weinheim p. IX of Preface.*
Slassi et. al. "Recent Progress in the 5-HT6 receptor antagonists for the treatment of CNS diseases" Expert Opinion on therapeutic Patents 2002, 12, 513-527.*
Sulfonyl Chlorides Available from Sigma-Aldrich (created by Examiner).*
Jorg Holenz, Petrus J. Pauwels, José Luis Diaz, Ramon Mercer, Xavier Codony and Helmut Buschmann "Medicinal chemistry strategies to 5-HT6 receptor ligands as potential cognitive enhancers and antiobesity agents" Drug Discovery Today 2006, 11, 283-299.*
Dorwald F. A. Side Reactions in Organic Synthesis, 2005, Wiley: VCH, Weinheim p. IX of Preface p. 1-15.*
Hauptman and Walter, Chem. Rev. 1962, 62, 347.*
Fieser and Fieser, Reagents for Organic Synthesis, vol. 1 Wiley: NY, 1974, p. 723-730.*
Mitchell and Lai Tetrahedron Letters 1980, 21, 2637.*

* cited by examiner

*Primary Examiner*—Rita J Desai
*Assistant Examiner*—David K O'Dell
(74) *Attorney, Agent, or Firm*—Gloria K. Szakiel; Scott Larsen; David Kurlandsky

(57) ABSTRACT

The present invention provides a compound of formula I and the use thereof in the therapeutic treatment of a central nervous system disorder related to or affected by the 5-HT6 receptor.

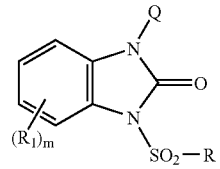

(I)

12 Claims, No Drawings

SULFONYLDIHYDROBENZIMIDAZOLONE COMPOUNDS AS 5-HYDROXYTRYPTAMINE-6 LIGANDS

This application claims the benefit under 35 U.S.C. §119 (e) to co-pending U.S. provisional application No. 60/489,417, filed Jul. 23, 2003, which is hereby incorporated by reference in its entirety.

BACKGROUND OF THE INVENTION

Serotonin (5-Hydroxytryptamine)(5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320-327) and subsequently from human tissue (Kohen, R.; Metcalf, M. A.; Khan, N.; Druck, T.; Huebner, K.; Sibley, D. R. *Journal of Neurochemistry* 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268-276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

One potential therapeutic use of modulators of 5-HT6 receptor function is in the enhancement of cognition and memory in human diseases such as Alzheimer's. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; El Mestikawy, S. *Brain Research,* 1997, 746, 207-219). The ability of known 5-HT6 receptor ligands to enhance cholinergic transmission also supported the potential cognition use (Bentley, J. C.; Boursson, A.; Boess, F. G.; Kone, F. C.; Marsden, C. A.; Petit, N.; Sleight, A. J. *British Journal of Pharmacology,* 1999, 126(7), 1537-1542). Studies have found that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT6 ligands in cognition (Dawson, L. A.; Nguyen, H. Q.; Li, P. *British Journal of Pharmacology,* 2000, 130(1), 23-26). Animal studies of memory and learning with a known selective 5-HT6 antagonist have found positive indications (Rogers, D. C.; Hatcher, P. D.; Hagan, J. J. *Society of Neuroscience,* *Abstracts* 2000, 26, 680 and Foley, A. G. et al, Neuropsychopharmacology, 2004, 29(1), 93-100.

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901-5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612).

Taken together, the above studies strongly suggest that compounds which are 5-HT6 receptor modulators, i.e. ligands, may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

SUMMARY OF THE INVENTION

The present invention provides a compound of formula I (I)

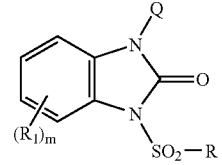

wherein
Q is

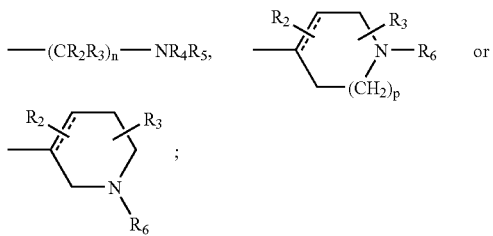

R is an optionally substituted $C_1$-$C_6$ alkyl, $C_3$-$C_7$ cycloalkyl, naphthyl or heteroaryl group or an optionally substituted 8- to 13-membered bicyclic or tricyclic ring system having a N atom at the bridgehead and optionally containing 1, 2 or 3 additional heteroatoms selected from N, O or S;

$R_1$ is halogen, CN, $OCO_2R_9$, $CO_2R_{10}$, $CONR_{11}R_{12}$, $SO_xR_{13}$, $NR_{14}R_{15}$, $OR_{16}$, $COR_{17}$ or a $C_1$-$C_6$alkyl, $C_2$-$C_6$alkenyl, $C_2$-$C_6$alkynyl, $C_3$-$C_7$ cycloalkyl, aryl or heteroaryl group each optionally substituted;

m is 0 or an integer of 1, 2 or 3;

$R_2$ and $R_3$ are each independently H or an optionally substituted $C_1$-$C_6$alkyl group;

n is an integer of 2, 3, 4 or 5;

p is 0 or an integer of 1 or 2;

$R_4$ and $R_5$ are each independently H or a $C_1$-$C_6$alkyl, $C_2$-$C_6$alkenyl, $C_2$-$C_6$alkynyl, $C_3$-$C_7$ cycloalkyl, cycloheteroalkyl, aryl or heteroaryl group each optionally substituted or $R_4$ and $R_5$ may be taken together with the atom to which they are attached to form an optionally substituted 5- to 8-membered ring optionally containing an additional heteroatom selected from O, $NR_7$ or $SO_x$;

$R_6$ and $R_7$ are each independently H or a $C_1$-$C_6$alkyl, $C_2$-$C_6$alkenyl, $C_2$-$C_6$alkynyl, $C_3$-$C_6$cycloalkyl or cycloheteroalkyl group each optionally substituted;

$R_9$, $R_{10}$, $R_{13}$, $R_{16}$ and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{11}$ and $R_{12}$ are each independently H or an optionally substituted $C_1$-$C_6$alkyl group or $R_{11}$ and $R_{12}$ may be taken together with the atom to which they are attached to form a 5- to 7-membered ring optionally containing another heteroatom selected from O, $NR_8$ or $SO_x$;

$R_{14}$, and $R_{15}$ are each independently H or an optionally substituted $C_1$-$C_4$alkyl group or $R_{14}$ and $R_{15}$ may be taken together with the atom to which they are attached to form a 5- to 7-membered ring optionally containing another heteroatom selected from O, $NR_8$ or $SO_x$;

$R_8$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted;

x is 0 or an integer of 1 or 2; and

-----represents a single bond or a double bond; or a stereoisomer thereof or a pharmaceutically acceptable salt thereof.

The present invention also provides methods and compositions useful in the treatment of central nervous system disorders.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104-109, Pharma Press Ltd.

Surprisingly, it has now been found that sulfonyldihydrobenzimidazolone compounds of formula I demonstrate 5-HT6 affinity along with significant sub-type selectivity. Advantageously, said formula I compounds are effective therapeutic agents for the treatment of central nervous system (CNS) disorders associated with or affected by the 5-HT6 receptor. Accordingly, the present invention provides sulfonyldihydrobenzimidazolone compounds of formula I

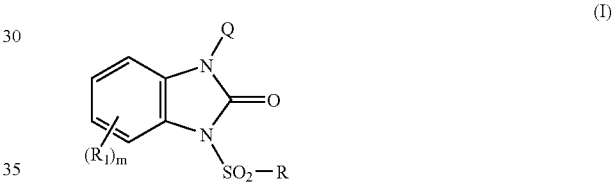

wherein
Q is

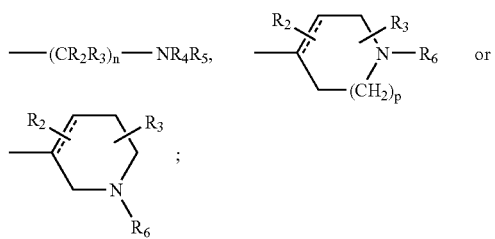

R is an optionally substituted $C_1$-$C_6$ alkyl, $C_3$-$C_7$ cycloalkyl, naphthyl or heteroaryl group or an optionally substituted 8- to 13-membered bicyclic or tricyclic ring system having a N atom at the bridgehead and optionally containing 1, 2 or 3 additional heteroatoms selected from N, O or S;

$R_1$ is halogen, CN, $OCO_2R_9$, $CO_2R_{10}$, $CONR_{11}R_{12}$, $SO_xR_{13}$, $NR_{14}R_{15}$, $OR_{16}$, $COR_{17}$ or a $C_1$-$C_6$alkyl, $C_2$-$C_6$alkenyl, $C_2$-$C_6$alkynyl, $C_3$-$C_7$cycloalkyl, aryl or heteroaryl group each optionally substituted;

m is 0 or an integer of 1, 2 or 3;

$R_2$ and $R_3$ are each independently H or an optionally substituted $C_1$-$C_6$alkyl group;

n is an integer of 2, 3, 4 or 5;

p is 0 or an integer of 1 or 2;

$R_4$ and $R_5$ are each independently H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted or $R_4$ and $R_5$ may be taken together with the atom to which they are attached to form an optionally substituted 5- to 8-membered ring optionally containing an additional heteroatom selected from O, $NR_7$ or $SO_x$;

$R_6$ and $R_7$ are each independently H or a $C_1$-$C_6$alkyl, $C_2$-$C_6$alkenyl, $C_2$-$C_6$alkynyl, $C_3$-$C_6$cycloalkyl or cycloheteroalkyl group each optionally substituted;

$R_9$, $R_{10}$, $R_{13}$, $R_{16}$ and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{11}$ and $R_{12}$ are each independently H or an optionally substituted $C_1$-$C_6$alkyl group or $R_{11}$ and $R_{12}$ may be taken together with the atom to which they are attached to form a 5- to 7-membered ring optionally containing another heteroatom selected from O, $NR_8$ or $SO_x$;

$R_{14}$, and $R_{15}$ are each independently H or an optionally substituted $C_1$-$C_4$alkyl group or $R_{14}$ and $R_{15}$ may be taken together with the atom to which they are attached to form a 5- to 7-membered ring optionally containing another heteroatom selected from O, $NR_8$ or $SO_x$;

$R_8$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted;

x is 0 or an integer of 1 or 2; and

----- represents a single bond or a double bond; or a stereoisomer thereof or a pharmaceutically acceptable salt thereof.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR', O or S; and R' is H or an optional substituent as described hereinbelow:

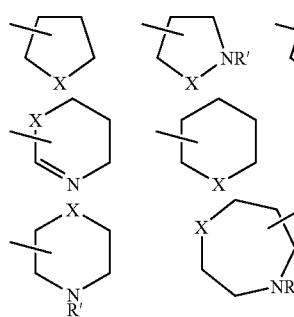

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein W is NR', O or S; and R' is H or an optional substituent as described hereinbelow:

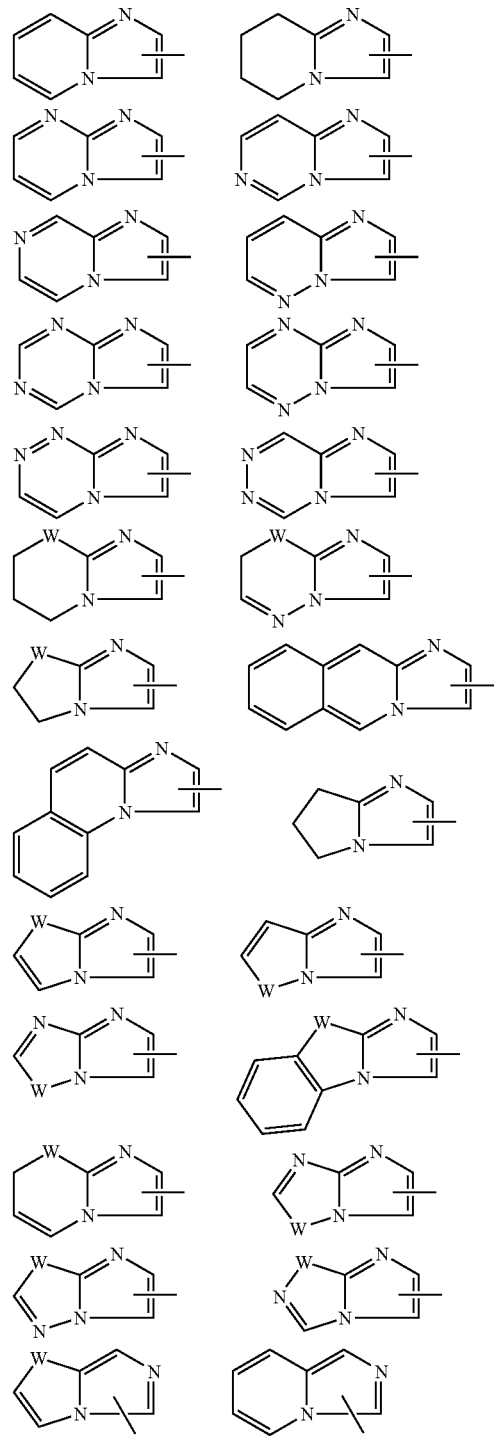

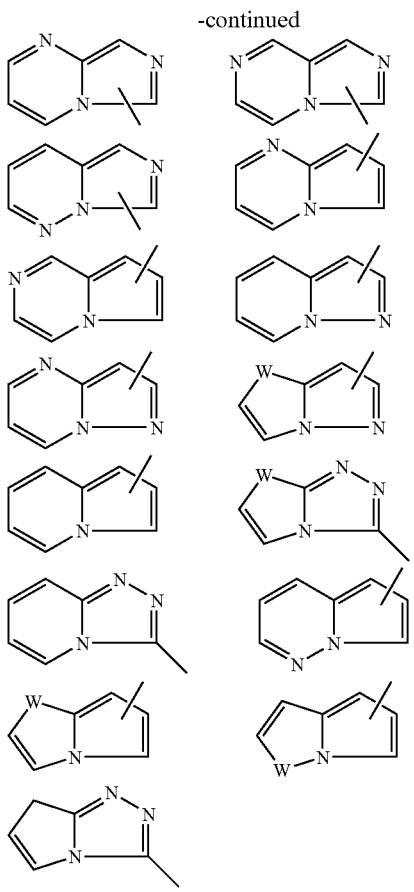

In the specification and claims, when the terms $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl are designated as being optionally substituted, the substituent groups which are optionally present may be one or more of those customarily employed in the development of pharmaceutical compounds, or the modification of such compounds, to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylaminocarbonyl, phenyl, phenoxy, benzyl, benzyloxy, heteroaryl, indolyl, heterocyclyl or cycloalkyl groups, preferably halogen atoms or lower alkyl or lower alkoxy groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein R is an optionally substituted naphthyl or heteroaryl group or an optionally substituted 8- to 13-membered bicyclic or tricyclic ring system having a N atom at the bridgehead and optionally containing 1, 2 or 3 additional heteroatoms selected from N, O or S. Another group of preferred compounds of the invention are those formula I compounds wherein Q is

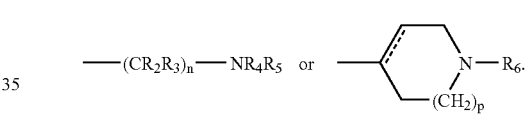

More preferred compounds of the invention are those compounds of formula I wherein R is an optionally substituted naphthyl, thienyl, benzothienyl or imidazo-[2,1-b][1,3] thiazolyl group. Another group of more preferred compounds of formula I are those compounds wherein Q is

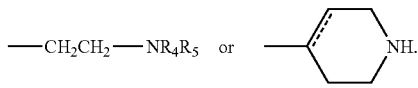

Among the preferred compounds of the invention are:

1-[(5-chlorothien-2-yl)sulfonyl]-3-[2-(dimethylamino) ethyl]-1,3-dihydro-2H-benzimidazol-2-one;

1-[(6-chloroimidazo[2,1-b][1,3]thiazol-5-yl)sulfonyl]-3-[2-(dimethylamino)ethyl]-1,3-dihydro-2H-benzimidazol-2-one;

1-[2-(dimethylamino)ethyl]-3-(2-naphthylsulfonyl)-1,3-dihydro-2H-benzimidazol-2-one;

1-[2-(dimethylamino)ethyl]-3-[5-chloro-3-methyl-benzo[b] thiophene-2-sulfonyl]-1,3-dihydro-2H-benzimidazol-2-one;

1-[(2-chloroimidazo[2,1-b]pyridin-3-yl)sulfonyl]-3-[2-(dimethylamino)ethyl]-1,3-dihydro-2H-benzimidazol-2-one;

1-[(2,6-dichloroimidazo[2,1-b][1,3]thiazol-5-yl)sulfonyl]-3-[2-(dimethylamino)ethyl]-1,3-dihydro-2H-benzimidazol-2-one;

1-[(5-bromothien-2-yl)sulfonyl]-3-[2-(dimethylamino)
ethyl]-1,3-dihydro-2H-benzimidazol-2-one;
1-[(2,5-dichlorothien-3-yl)sulfonyl]-3-[2-(dimethylamino)
ethyl]-1,3-dihydro-2H-benzimidazol-2-one;
1-[2-(dimethylamino)ethyl]-3-(1-naphthylsulfonyl)-1,3-dihydro-2H-benzimidazol-2-one;
1-(2-aminoethyl)-3-[(5-chlorothien-2-yl)sulfonyl]-1,3-dihydro-2H-benzimidazol-2-one;
1-(2-aminoethyl)-3-[(6-chloroimidazo[2,1-b][1,3]thiazol-5-yl)sulfonyl]-1,3-dihydro-2H-benzimidazol-2-one;
1-(2-aminoethyl)-3-(2-naphthylsulfonyl)-1,3-dihydro-2H-benzimidazol-2-one;
1-(2-aminoethyl)-3-[(5-bromothien-2-yl)sulfonyl]-1,3-dihydro-2H-benzimidazol-2-one;
1-(2-naphthylsulfonyl)-3-piperidin-4-yl-1,3-dihydro-2H-benzimidazol-2-one;
1-[(5-chlorothien-2-yl)sulfonyl]-3-piperidin-4-yl-1,3-dihydro-2H-benzimidazol-2-one;
1-[(5-bromothien-2-yl)sulfonyl]-3-piperidin-4-yl-1,3-dihydro-2H-benzimidazol-2-one;
1-[(4,5-dichlorothien-2-yl)sulfonyl]-3-piperidin-4-yl-1,3-dihydro-2H-benzimidazol-2-one;
1-[(2,5-dichlorothien-3-yl)sulfonyl]-3-piperidin-4-yl-1,3-dihydro-2H-benzimidazol-2-one;
1-[(4,5-dibromothien-2-yl)sulfonyl]-3-piperidin-4-yl-1,3-dihydro-2H-benzimidazol-2-one;
1-[(3-bromo-5-chlorothien-2-yl)sulfonyl]-3-piperidin-4-yl-1,3-dihydro-2H-benzimidazol-2-one;
1-[(4-bromo-5-chlorothien-2-yl)sulfonyl]-3-piperidin-4-yl-1,3-dihydro-2H-benzimidazol-2-one;
1-[(4-bromo-2,5-dichlorothien-3-yl)sulfonyl]-3-piperidin-4-yl-1,3-dihydro-2H-benzimidazol-2-one;
1-[(5-chloro-3-methyl-1-benzothien-2-yl)sulfonyl]-3-piperidin-4-yl-1,3-dihydro-2H-benzimidazol-2-one;
1-[(6-chloroimidazo[2,1-b][1,3]thiazol-5-yl)sulfonyl]-3-piperidin-4-yl-1,3-dihydro-2H-benzimidazol-2-one;
1-[(2,6-dichloroimidazo[2,1-b][1,3]thiazol-5-yl)sulfonyl]-3-piperidin-4-yl-1,3-dihydro-2H-benzimidazol-2-one;
1-[(2-chloroimidazo[1,2-a]pyridin-3-yl)sulfonyl]-3-piperidin-4-yl-1,3-dihydro-2H-benzimidazol-2-one;
1-[(1,2-dimethyl-1H-imidazol-4-yl)sulfonyl]-3-piperidin-4-yl-1,3-dihydro-2H-benzimidazol-2-one;
1-[(5-chloro-1,3-dimethyl-1H-pyrazol-4-yl)sulfonyl]-3-piperidin-4-yl-1,3-dihydro-2H-benzimidazol-2-one;
1-[(3,5-dimethylisoxazol-4-yl)sulfonyl]-3-piperidin-4-yl-1,3-dihydro-2H-benzimidazol-2-one;
1-[(2,1,3-benzothiadiazol-4-yl)sulfonyl]-3-piperidin-4-yl-1,3-dihydro-2H-benzimidazol-2-one;
1-(2-naphthylsulfonyl)-3-(1,2,3,6-tetrahydropyridin-4-yl)-1,3-dihydro-2H-benzimidazol-2-one;
1-[(5-chlorothien-2-yl)sulfonyl]-3-(1,2,3,6-tetrahydropyridin-4-yl)-1,3-dihydro-2H-benzimidazol-2-one;
1-[(5-bromothien-2-yl)sulfonyl]-3-(1,2,3,6-tetrahydropyridin-4-yl)-1,3-dihydro-2H-benzimidazol-2-one;
1-[(4,5-dichlorothien-2-yl)sulfonyl]-3-(1,2,3,6-tetrahydropyridin-4-yl)-1,3-dihydro-2H-benzimidazol-2-one;
1-[(2,5-dichlorothien-3-yl)sulfonyl]-3-(1,2,3,6-tetrahydropyridin-4-yl)-1,3-dihydro-2H-benzimidazol-2-one;
1-[(4,5-dibromothien-2-yl)sulfonyl]-3-(1,2,3,6-tetrahydropyridin-4-yl)-1,3-dihydro-2H-benzimidazol-2-one;
1-[(3-bromo-5-chlorothien-2-yl)sulfonyl]-3-(1,2,3,6-tetrahydropyridin-4-yl)-1,3-dihydro-2H-benzimidazol-2-one;
1-[(4-bromo-5-chlorothien-2-yl)sulfonyl]-3-(1,2,3,6-tetrahydropyridin-4-yl)-1,3-dihydro-2H-benzimidazol-2-one;
1-[(4-bromo-2,5-dichlorothien-3-yl)sulfonyl]-3-(1,2,3,6-tetrahydropyridin-4-yl)-1,3-dihydro-2H-benzimidazol-2-one;
1-[(5-chloro-3-methyl-1-benzothien-2-yl)sulfonyl]-3-(1,2,3,6-tetrahydropyridin-4-yl)-1,3-dihydro-2H-benzimidazol-2-one;
1-[(6-chloroimidazo[2,1-b][1,3]thiazol-5-yl)sulfonyl]-3-(1,2,3,6-tetrahydropyridin-4-yl)-1,3-dihydro-2H-benzimidazol-2-one;
1-[(2,6-dichloroimidazo[2,1-b][1,3]thiazol-5-yl)sulfonyl]-3-(1,2,3,6-tetrahydropyridin-4-yl)-1,3-dihydro-2H-benzimidazol-2-one;
1-[(2-chloroimidazo[1,2-a]pyridin-3-yl)sulfonyl]-3-(1,2,3,6-tetrahydropyridin-4-yl)-1,3-dihydro-2H-benzimidazol-2-one;
1-[(1,2-dimethyl-1H-imidazol-4-yl)sulfonyl]-3-(1,2,3,6-tetrahydropyridin-4-yl)-1,3-dihydro-2H-benzimidazol-2-one;
1-[(5-chloro-1,3-dimethyl-1H-pyrazol-4-yl)sulfonyl]-3-(1,2,3,6-tetrahydropyridin-4-yl)-1,3-dihydro-2H-benzimidazol-2-one;
1-[(3,5-dimethylisoxazol-4-yl)sulfonyl]-3-(1,2,3,6-tetrahydropyridin-4-yl)-1,3-dihydro-2H-benzimidazol-2-one;
1-(2,1,3-benzothiadiazol-4-ylsulfonyl)-3-(1,2,3,6-tetrahydropyridin-4-yl)-1,3-dihydro-2H-benzimidazol-2-one;

a stereoisomer thereof; and a pharmaceutically acceptable salt thereof.

Advantageously, the present invention provides a process for the preparation of a compound of formula I which comprises reacting a compound of formula II with a sulfonyl chloride, $ClSO_2$—R, in the presence of a base. The process is shown in flow diagram I.

Flow Diagram I

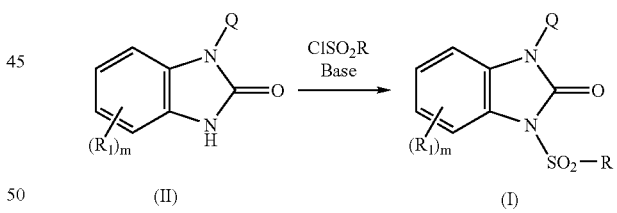

Bases suitable for use in the process of the invention include bases such as NaH, KOt-Bu, diisopropylethylamine, or any conventional base capable of removing a proton from a nitrogen atom.

Compounds of formula II may be prepared using conventional synthetic methods and, if required, standard separation or isolation techniques. For example, compounds of formula II may be readily prepared by reacting an ortho-halonitrobenzene of formula III with the appropriate amine of formula IV to give the corresponding nitro compound of formula V; reducing said formula V compound using a suitable reducing agent such as $SnCl_2$ or hydrazine and Raney-Nickel to give the diamine of formula VI; and cyclizing said formula VI compound with 1,1'-carbonyldiimidazole (CDI) to give the desired formula II compound. The reaction is shown in flow diagram II wherein X is Cl or F.

Flow Diagram II

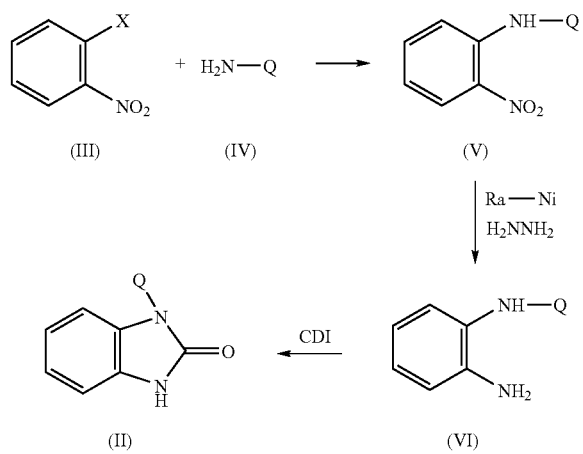

When the formula IV compound contains a Q group having a basic nitrogen atom, for example when Q is 4-piperidinyl, then said formula IV compound may be protected prior to the reactions shown in flow diagram I.

Protecting groups suitable for use in the reactions shown hereinabove include t-butyloxycarbonyl, benzyl, acetyl, benzyloxycarbonyl, or any conventional group known to protect a basic nitrogen in standard synthetic procedures.

Advantageously, the formula I compounds of the invention are useful for the treatment of CNS disorders relating to or affected by 5-HT6 receptor including mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician or the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The term NMR designates nuclear magnetic resonance. The terms HPLC and TLC designate high performance liquid chromatography and thin layer chromatography, respectively. The terms THF, DMF and EtOAc designate tetrahydrofuran, dimethyl formamide and ethyl acetate, respectively.

EXAMPLE 1

Preparation of N,N-Dimethyl-N'-(2-nitrophenyl)ethane-1,2-diamine

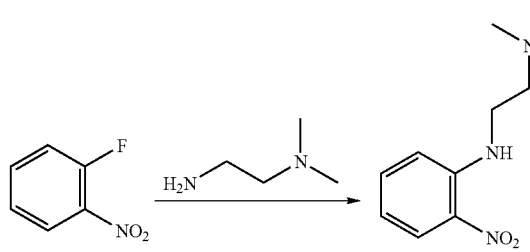

A mixture of 2-fluoro-nitrobenzene (2.8 g, 20 mmol) and N,N-dimethylethylenediamine (3.3 mL, 30 mmol) in isopropanol is heated at 90°-100° C. for 16 h, cooled to 0° C. and filtered. The filtercake is washed with cold isopropanol and air-dried to give the title compound as an orange solid, 3.83 g (92% yield), identified by HPLC and mass spectral analyses.

EXAMPLE 2

Preparation of N-[2-(Dimethylamino)ethyl]benzene-1,2-diamine

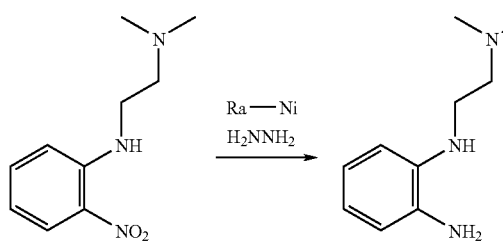

A mixture of N,N-dimethyl-N'-(2-nitrophenyl)ethane-1,2-diamine (3.83 g, 18.3 mmol) and Raney-Nickel (0.5 g) in methanol is treated dropwise with hydrazine (5 mL), stirred at room temperature until reaction is complete by TLC, treated with Celite and MgSO₄ and filtered. The filtercake is washed with methanol. The combined filtrate is concentrated in vacuo to give the title compound as a brown oil, 3.11 g (94% yield), identified by HPLC and mass spectral analyses.

EXAMPLE 3

Preparation of 1-[2-(Dimethylamino)ethyl]-1,3-dihydrobenzimidazol-2-one

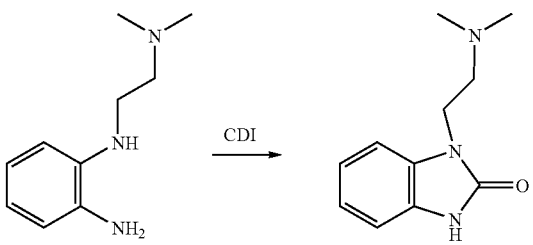

A mixture of N-[2-(dimethylamino)ethyl]benzene-1,2-diamine (3.11 g, 17.3 mmol) and 1,1-carbonyldiimidazole (CDI) (3.2 g, 19 mmol) are heated in DMF to 110°-120° C. until reaction is complete by TLC, cooled and extracted with EtOAc. The combined extracts are washed with water, dried over MgSO₄ and concentrated in vacuo. The resultant residue is purified by flash chromatography (silica gel, 94:5:1 CH₂Cl₂, methanol, concentrated NH₄OH as eluent) to give the title compound as a dark purple solid, 3.03 g (85% yield), identified by HPLC and mass spectral analyses.

EXAMPLE 4

Preparation of 1-[(5-Chlorothien-2-yl)sulfonyl]-3-[2-(dimethylamino)ethyl]-1,3-dihydro-2H-benzimidazol-2-one

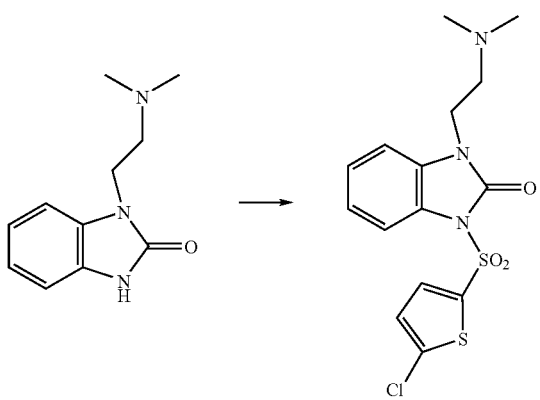

A solution of 1-[2-(dimethylamino)ethyl]-1,3-dihydrobenzimidazol-2-one (20 mg, 0.1 mmol) in THF at room temperature is treated with (5-chlorothien-2-yl)sulfonyl chloride (26 mg, 0.12 mmol) followed by diisopropylethylamine (25 uL, 0.2 mmol) and dimethylaminopyridine (5 mg), stirred at room temperature for 16 hours and concentrated in vacuo. The resultant residue is dissolved in a mixture of dimethylsulfoxide, methanol and water and purified by Gilson[1] preparative HPLC to give the title product, 16 mg, [M+H] 386, retention time (RT) 2.83 minutes.

[1] Gilson Preparative HPLC conditions: Gilson Preparative HPLC system; YMC Pro C18, 20 mm×50 mm ID, 5 uM column; 2 mL injection; Solvent A: 0.02% TFA/water; Solvent B:0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.

EXAMPLES 5-12

Preparation of 1-Arylsulfonyl-3-[2-(dimethylamino)ethyl]-1,3-dihydro-2H-benzimidazol-2-one Derivatives

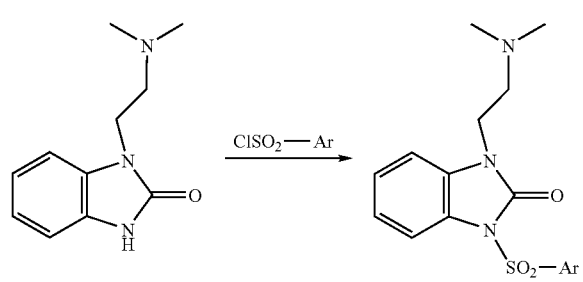

Using essentially the same procedures described in Example 4 hereinabove and employing the appropriate arylsulfonyl chloride, the compounds shown in Table I are prepared and identified by HPLC[2] and mass spectral analyses.

[2]HPLC Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% formic acid in water; Solvent B 0.02% formic acid in ACN; Gradient: Time 0: 10% B; 2.5 min 90% B; 3 min 90% B; Sample concentration: ~2.0 mM; Injection volume: 5 uL; Detection: 220 nm, 254 nm DAD.

TABLE I

| Ex. No. | R | Observed Ion | HPLC RT (min) |
|---|---|---|---|
| 5 | 6-chloroimidazo[2,1-b][1,3]thiazol-5-yl | 426[M + H] | 2.77 |
| 6 | 2-naphthyl | 396[M + H] | 2.88 |
| 7 | 5-chloro-3-methyl-benzo[b]thien-2-yl | 450[M+] | 3.11 |
| 8 | 2-chloroimidazo[2,1-b]pyridin-3-yl | 422[M + H] | 2.78 |
| 9 | 2,6-dichloroimidazo[2,1-b][1,3]thiazol-5-yl | 460[M+] | 2.91 |
| 10 | 5-bromothien-2-yl | 430[M+] | 2.87 |
| 11 | 2,5-dichlorothien-3-yl | 420[M+] | 1.93 |
| 12 | 1-naphthyl | 396[M + H] | 2.84 |

EXAMPLE 13

Preparation of N-[1-(2-Nitrophenyl)ethane]-1,2-diamine

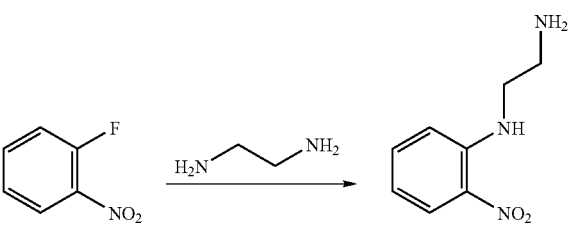

A mixture of 2-fluoronitrobenzene (2.8 g, 20 mmol) and ethylenediamine (4.1 mL, 60 mmol) in isopropanol is heated at 90°-100° C. for 16 h, cooled to 0° C. and filtered. The filtercake is washed with cold isopropanol and air-dried to give the title compound as a yellow solid, 2.3 g, (64% yield), identified by HPLC and mass spectral analyses.

EXAMPLE 14

Preparation of [2-(2-Nitrophenylamino)ethyl]carbamic acid t-butyl ester

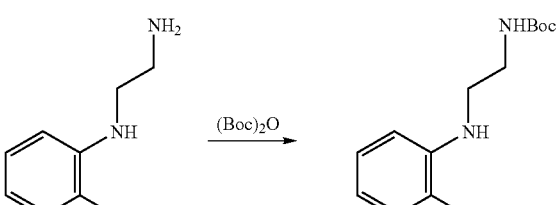

A solution of N-[1-(2-nitrophenyl)ethane]-1,2-diamine (2.3 g, 12.7 mmol) in 1:1 acetone/water is treated with $K_2CO_3$ (3.5 g, 25 mmol) and di-t-butoxy dicarbonyl [(Boc)$_2$O] (3.3 g, 15.2 mmol), stirred at room temperature for 3 h and concentrated in vacuo to remove the acetone. The aqueous residue is extracted with EtOAc. The combined extracts are dried over MgSO₄ and concentrated in vacuo to give the title compound as a yellow solid, 3.5 g (98% yield), identified by HPLC and mass spectral analyses.

EXAMPLE 15

Preparation of [2-(2-Aminophenylamino)ethyl]carbamic acid t-butyl ester

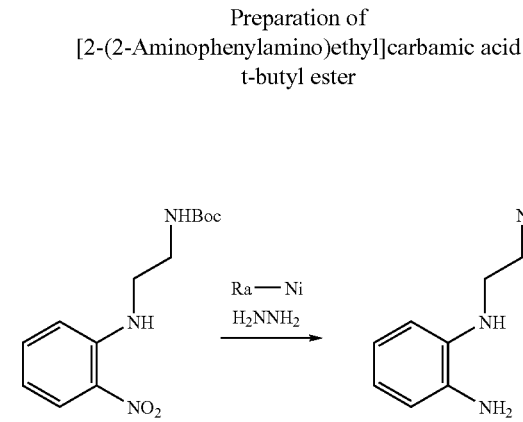

A mixture of [2-(2-nitrophenylamino)ethyl]carbamic acid t-butyl ester (6 g, 21.3 mmol) and Raney-Nickel (0.5 g) in methanol is treated dropwise with hydrazine (0.8 mL, 25 mmol), stirred at room temperature until reaction is complete by TLC, treated with Celite and MgSO₄ and filtered. The filtercake is washed with methanol. The filtrates are combined and concentrated in vacuo to give the title compound as a brown oil, 3.85 g (72% yield), identified by HPLC and mass spectral analyses.

EXAMPLE 16

Preparation of [2-(2-Oxo-2,3-dihydrobenzimidazol-1-yl)ethyl]-carbamic acid t-butyl ester

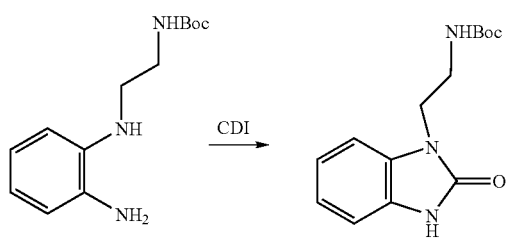

A mixture of [2-(2-aminophenylamino)ethyl]carbamic acid t-butyl ester (3.85 g, 15.3 mmol) and 1,1-carbonyldiimidazole (CDI) (2.73 g, 16.8 mmol) in DMF are heated at 110°-120° C. until reaction is complete by TLC, cooled and extracted with EtOAc. The combined extracts are washed with water, dried over MgSO₄ and concentrated in vacuo. The resultant residue is purified by flash chromatography (silica gel, 1:1 CH₂Cl₂: EtOAc as eluent) to give the title compound as a brown solid, 2.4 g (56% yield), identified by HPLC and mass spectral analyses.

EXAMPLE 17

Preparation of 1-(2-Aminoethyl)-3-[(5-chlorothien-2-yl)sulfonyl]-1,3-dihydro-2H-benzimidazol-2-one

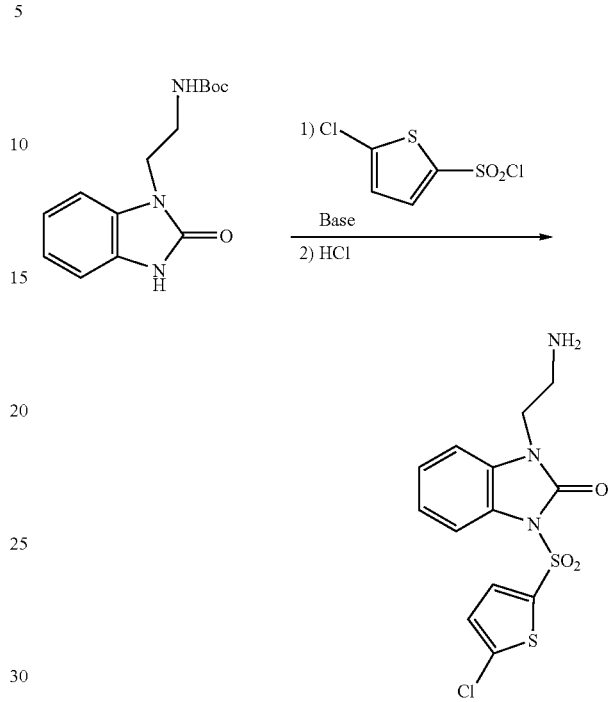

A solution of [2-(2-oxo-2,3-dihydrobenzimidazol-1-yl)ethyl]carbamic acid t-butyl ester (27 mg, 0.1 mmol) in THF at room temperature is treated with (5-chlorothien-2-yl)sulfonyl chloride (26 mg, 0.12 mmol) followed by diisopropylethylamine (25 uL, 0.2 mmol) and 4-dimethylaminopyridine (5 mg), stirred at room temperature for 16 h and concentrated in vacuo. The resultant residue is dissolved in THF, treated with HCl in dioxane (4 N) (1 mL), stirred for 4 h and concentrated in vacuo. This residue is dissolved in a mixture of DMSO, methanol and water and purified by Gilson[1] preparative HPLC to give the title product, 10 mg, [M+H] 358, retention time (RT) 2.18 minutes.

[1] Gilson Preparative HPLC conditions: Gilson Preparative HPLC system; YMC Pro C18, 20 mm×50 mm ID, 5 uM column; 2 mL injection; Solvent A: 0.02% TFA/water; Solvent B:0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.

EXAMPLES 18-20

Preparation of 1-(2-Aminoethyl)-3-(arylsulfonyl)-1,3-dihydro-2H-benzimidazol-2-one Derivatives

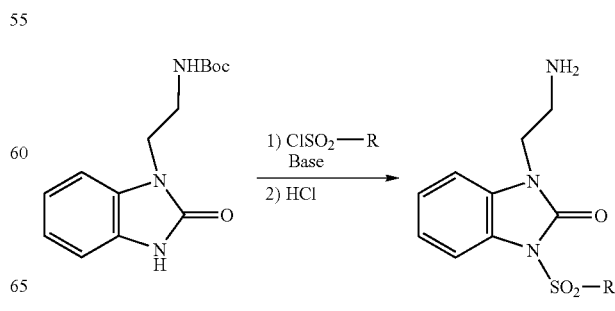

Using essentially the same procedure described in Example 17 hereinabove and employing the appropriate arylsulfonyl chloride, the compounds shown in Table II are obtained and identified by HPLC[2] and mass spectral analyses.

[2]HPLC Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% formic acid in water; Solvent B 0.02% formic acid in ACN; Gradient: Time 0: 10% B; 2.5 min 90% B; 3 min 90% B; Sample concentration: ~2.0 mM; Injection volume: 5 uL; Detection: 220 nm, 254 nm DAD.

TABLE II

| Ex. No. | R | Observed Ion | HPLC RT (min) |
|---|---|---|---|
| 18 | 6-chloroimidazo[2,1-b][1,3]thiazol-5-yl | 398 [M + H] | 2.1 |
| 19 | 2-naphthyl | 368 [M + H] | 2.32 |
| 20 | 5-bromothien-2-yl | 402 [M + H] | 2.21 |

EXAMPLE 21

Preparation of 4-(2-Oxo-2,3-dihydrobenzimidazol-1-yl)piperidine-1-carboxylic acid t-butyl ester

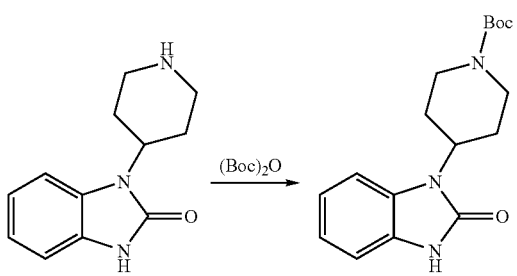

A solution of 1-piperidin-4-yl-1,3-dihydrobenzimidazol-2-one (5 g, 23 mmol) in acetone is treated with di-t-butoxydicarbonyl [(Boc)₂O] (5.0 g, 23 mmol), stirred at room temperature for 3 h and concentrated in vacuo to give the title compound, 7.2 g, identified by HPLC and mass spectral analyses.

EXAMPLE 22

Preparation of 3-(Naphth-2-ylsulfonyl)-1-piperidin-4-yl-1,3-dihydrobenzimidazol-2-one

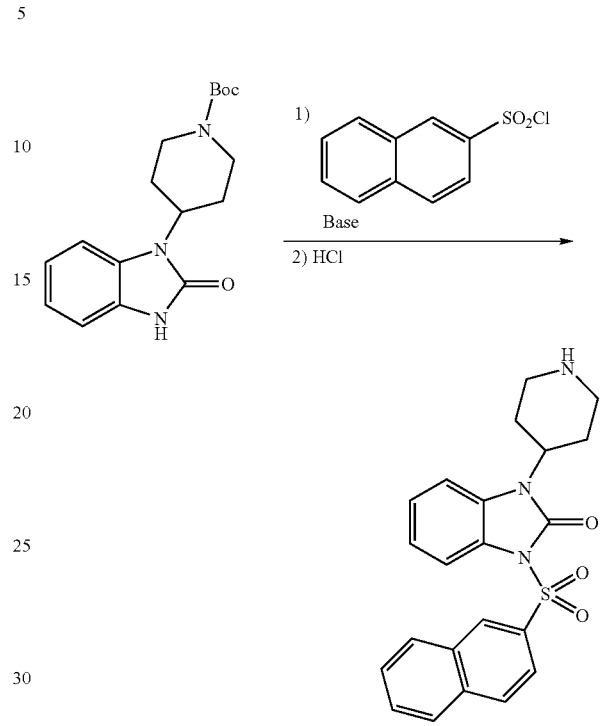

A solution of 4-(2-oxo-2,3-dihydrobenzimidazol-1-yl)piperidine-1-carboxylic acid t-butyl ester (64 mg, 0.2 mmol) in CH₂Cl₂ at room temperature is treated with 2-naphthylsulfonyl chloride (50 mg, 0.2 mmol) followed by diisopropylethylamine (174 uL, 1.0 mmol) and 4-dimethylaminopyridine (24 mg, 0.2 mmol), stirred at 60° C. for 16 h and concentrated in vacuo. The resultant residue is dissolved in THF, treated with HCl in dioxane (4 N) (1 mL), stirred for 4 h and concentrated in vacuo. This residue is dissolved in a mixture of DMSO, methanol and water and purified by Gilson[1] preparative HPLC to give the title product, 24 mg, [M+H] 408, retention time (RT) 1.89 minutes.

[1]Gilson Preparative HPLC conditions: Gilson Preparative HPLC system; YMC Pro C18, 20 mm×50 mm ID, 5 uM column; 2 mL injection; Solvent A: 0.02% TFA/water; Solvent B: 0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.

EXAMPLES 23-38

Preparation of 3-Arylsulfonyl-1-piperidin-4-yl-1,3-dihydrobenzimidazol-2-one Derivatives

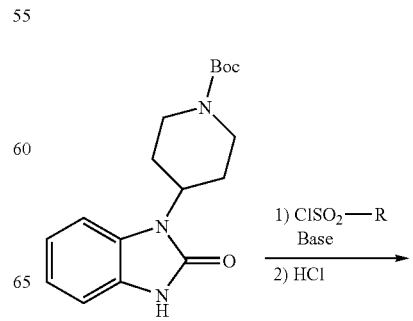

EXAMPLES 39-55

Preparation of 3-Arylsulfonyl-1-(1,2,3,6-tetrahydropyridin-4-yl)-1,3-dihydrobenzimidazol-2-one Derivatives

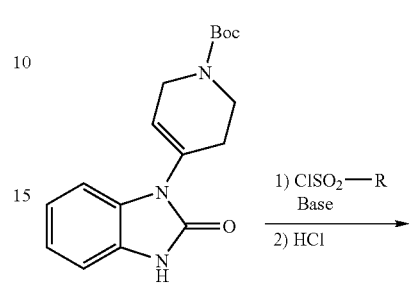

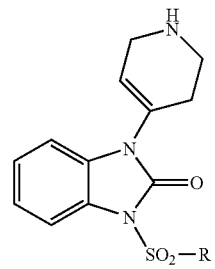

Using essentially the same procedure described in Example 22 hereinabove and employing 1-(1,2,3,6-tetrahydropyridin-4-yl)-1,3-dihydrobenzimidazol-2-one as substrate and the appropriate arylsulfonyl chloride, the compounds shown in Table IV are obtained and identified by HPLC[1] and mass spectral analyses.

[1]HPLC conditions are the same as those used for Table III

TABLE IV

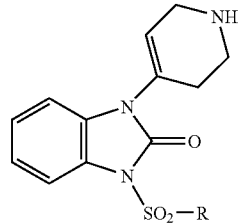

| Ex. No. | R | Observed Ion | HPLC RT (min) |
|---|---|---|---|
| 39 | 2-naphthyl | 406 [M + H] | 1.84 |
| 40 | 5-chlorothien-2-yl | 396 [M + H] | 2.08 |
| 41 | 5-bromothien-2-yl | 441 [M + H] | 2.11 |
| 42 | 4,5-dichlorothien-2-yl | 430 [M+] | 2.25 |
| 43 | 2,5-dichlorothien-3-yl | 430 [M+] | 2.18 |
| 44 | 4,5-dibromothien-2-yl | 520 [M + H] | 2.29 |
| 45 | 3-bromo-5-chlorothien-2-yl | 475 [M + H] | 2.2 |
| 46 | 4-bromo-5-chlorothien-2-yl | 475 [M + H] | 2.28 |
| 47 | 4-bromo-2,5-dichlorothien-3-yl | 510 [M + H] | 2.31 |
| 48 | 5-chloro-3-methyl-1-benzothien-2-yl | 460 [M + H] | 2.43 |
| 49 | 6-chloroimidazo[2,1-b][1,3]thiazol-5-yl | 436 [M + H] | 2.02 |
| 50 | 2,6-dichloroimidazo[2,1-b][1,3]thiazol-5-yl | 431 [M + H] | 2.16 |
| 51 | 2-chloroimidazo[1,2-a]pyridin-3-yl | 430 [M + H] | 2.02 |
| 52 | 1,2-dimethyl-1H-imidazol-4-yl | 374 [M + H] | 1.6 |
| 53 | 5-chloro-1,3-dimethyl-1H-pyrazol-4-yl | 408 [M + H] | 1.9 |
| 54 | 3,5-dimethylisoxazol-4-yl | 375 [M + H] | 1.91 |
| 55 | 2,1,3-benzothiadiazol-4-yl | 414 [M + H] | 1.9 |

-continued

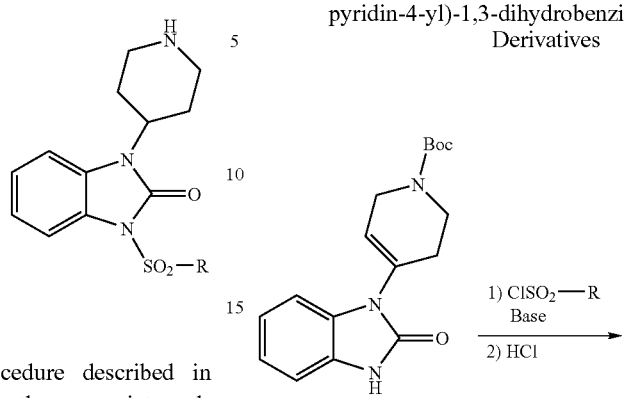

Using essentially the same procedure described in Example 22 hereinabove and employing the appropriate arylsulfonyl chloride, the compounds shown in Table III are obtained and identified by HPLC[1] and mass spectral analyses.

[1]HPLC Conditions: HP 1100 HPLC system; Waters Xterra MS C18, 2 mm (i.d.)×50 mm (length), 3.5 um column, set at 50° C.; Flow rate 1.0 mL/min; Solvent A: 0.02% formic acid in water; Solvent B 0.02% formic acid in ACN; Gradient: Time 0: 10% B; 2.5 min 90% B; 3 min 90% B; Sample concentration: ~2.0 mM; Injection volume: 5 uL; Detection: 220 nm, 254 nm DAD.

TABLE III

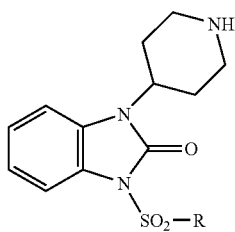

| Ex. No. | R | Observed Ion | HPLC RT (min) |
|---|---|---|---|
| 23 | 5-chlorothien-2-yl | 398 [M + H] | 2.07 |
| 24 | 5-bromothien-2-yl | 442 [M+] | 2.05 |
| 25 | 2,3-dichlorothien-5-yl | 432 [M+] | 2.24 |
| 26 | 2,5-dichlorothien-3-yl | 432 [M+] | 2.15 |
| 27 | 2,3-dibromothien-5-yl | 522 [M + H] | 2.29 |
| 28 | 4-bromo-2-chlorothien-5-yl | 476 [M+] | 2.19 |
| 29 | 3-bromo-2-chlorothien-5-yl | 476 [M+] | 2.27 |
| 30 | 3-bromo-2,5-dichlorothien-4-yl | 512 [M + H] | 2.23 |
| 31 | 5-chloro-3-methylbenzothien-2-yl | 462 [M + H] | 2.41 |
| 32 | 6-chloroimidazo[2,1-b][1,3]thiazol-5-yl | 438 [M+] | 2.02 |
| 33 | 2,6-dichloroimidazo[2,1-b][1,3]thiazol-5-yl | 472 [M+] | 2.16 |
| 34 | 2-chloroimidazo[1,2-a]pyridin-3-yl | 432 [M + H] | 2.02 |
| 35 | 1,2-dimethyl-1H-imidazol-4-yl | 376 [M + H] | 1.6 |
| 36 | 5-chloro-1,3-dimethyl-1H-pyrazol-4-yl | 410 [M + H] | 1.87 |
| 37 | 3,5-dimethylisoxazol-4-yl | 377 [M + H] | 1.91 |
| 38 | 2,1,3-benzothiadiazol-4-yl | 416 [M + H] | 1.91 |

EXAMPLE 56

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM $MgCl_2$ and 0.5 mM EDTA and 20 μl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table V, below.

TABLE V

| Test Compound (Ex. No.) | 5-HT6 binding Ki (nM) |
|---|---|
| 4 | 43 |
| 5 | 20 |
| 6 | 17 |
| 10 | 40 |
| 17 | 26 |
| 18 | 6 |
| 19 | 23 |
| 20 | 26 |
| 22 | 20 |
| 23 | 20 |
| 24 | 5 |
| 25 | 32 |
| 26 | 34 |
| 27 | 27 |
| 27 | 37 |
| 29 | 20 |
| 30 | 42 |
| 31 | 80 |
| 32 | 46 |
| 33 | 23 |
| 34 | 77 |
| 38 | 45 |
| 39 | 6 |
| 40 | 5 |
| 41 | 4 |
| 42 | 15 |
| 43 | 9 |
| 45 | 10 |
| 46 | 9 |
| 48 | 49 |
| 49 | 2 |
| 50 | 18 |
| 51 | 19 |
| 52 | 133 |
| 53 | 28 |
| 54 | 51 |
| 55 | 12 |

| Comparative Examples | 5-HT6 binding Ki |
|---|---|
| Clozapine | 6.0 |
| Loxapine | 41.4 |
| Bromocriptine | 23.0 |
| Methiothepin | 8.3 |
| Mianserin | 44.2 |
| Olanzepine | 19.5 |

What is claimed is:

1. A compound of formula I

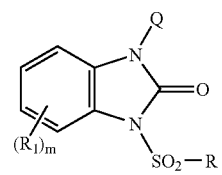

(I)

wherein

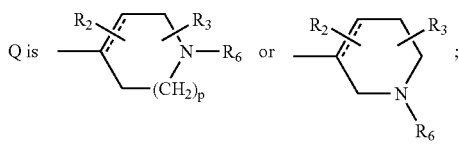

R is an optionally substituted naphthyl, thienyl, benzothienyl, imidazo[2,1-b][1,3]thiazolyl, imidazo[1,2-a]pyridinyl, imidazolyl, pyrazolyl, isoxazolyl, benzothiadiazolyl or pyridinyl group;
$R_1$ is halogen, CN, $OCO_2R_9$, $CO_2R_{10}$, $CONR_{11}R_{12}$, $SO_xR_{13}$, $NR_{14}R_{15}$, $OR_{16}$, $COR_{17}$ or an optionally substituted $C_1$-$C_6$alkyl group;
m is 0 or an integer of 1, 2 or 3;
$R_2$ and $R_3$ are each independently H or $C_1$-$C_6$alkyl group;
p is an integer of 1;
$R_6$ is H or a $C_1$-$C_6$alkyl;
$R_9$, $R_{10}$, $R_{13}$, $R_{16}$ and $R_{17}$ are each independently H or optionally substituted $C_1$-$C_6$alkyl;
$R_{11}$ and $R_{12}$ are each independently H or an optionally substituted $C_1$-$C_6$alkyl group;
$R_{14}$, and $R_{15}$ are each independently H or and optionally substituted $C_1$-$C_4$alkyl group;
x is 0 or an integer of 1 or 2; and
----- represents a single bond or a double bond; or
a stereoisomer thereof or a pharmaceutically acceptable salt thereof;
wherein the substituted groups which are optionally present are selected from the group consisting of hydrogen, halogen atoms, nitro, cyano, hydroxyl, alkyl, haloalkyl, alkoxy, haloalkoxy, amino, alkylamino, dialkylamino, carboxyl, alkanoyl, alkylthio, alkylsulphonyl, carbamoyl, and alkylaminocarbonyl groups.

2. The compound according to claim 1 wherein Q is

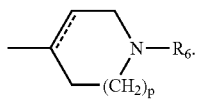

3. The compound according to claim 2 wherein R is an optionally substituted naphthyl, thienyl, benzothienyl or imidazo[2,1-b][1,3]thiazolyl group.
4. The compound according to claim 2 wherein $R_6$ is H.
5. The compound according to claim 3 wherein Q is

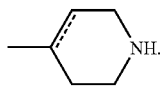

6. The compound according to claim 1 selected from the group consisting of:
1-[(2-chloroimidazo[2,1-b]pyridin-3-yl)sulfonyl]-3-[2-(dimethylamino)ethyl]-1,3-dihydro-2H-benzimidazol-2-one;
1-(2-naphthylsulfonyl)-3-piperidin-4-yl-1,3-dihydro-2H-benzimidazol-2-one;
1-[(5-chlorothien-2-yl)sulfonyl]-3-piperidin-4-yl-1,3-dihydro-2H-benzimidazol-2-one;
1-[(5-bromothien-2-yl)sulfonyl]-3-piperidin-4-yl-1,3-dihydro-2H-benzimidazol-2-one;
1-[(4,5-dichlorothien-2-yl)sulfonyl]-3-piperidin-4-yl-1,3-dihydro-2H-benzimidazol-2-one;
1-[(2,5-dichlorothien-3-yl)sulfonyl]-3-piperidin-4-yl-1,3-dihydro-2H-benzimidazol-2-one;
1-[(4,5-dibromothien-2-yl)sulfonyl]-3-piperidin-4-yl-1,3-dihydro-2H-benzimidazol-2-one;
1-[(3-bromo-5-chlorothien-2-yl)sulfonyl]-3-piperidin-4-yl-1,3-dihydro-2H-benzimidazol-2-one;
1-[(4-bromo-5-chlorothien-2-yl)sulfonyl]-3-piperidin-4-yl-1,3-dihydro-2H-benzimidazol-2-one;
1-[(4-bromo-2,5-dichlorothien-3-yl)sulfonyl]-3-piperidin-4-yl-1,3-dihydro-2H-benzimidazol-2-one;
1-[(5-chloro-3-methyl-1-benzothien-2-yl)sulfonyl]-3-piperidin-4-yl-1,3-dihydro-2H-benzimidazol-2-one;
1-[(6-chloroimidazo[2,1-b][1,3]thiazol-5-yl)sulfonyl]-3-piperidin-4-yl-1,3-dihydro-2H-benzimidazol-2-one;
1-[(2,6-dichloroimidazo[2,1-b][1,3]thiazol-5-yl)sulfonyl]-3-piperidin-4-yl-1,3-dihydro-2H-benzimidazol-2-one;
1-[(2-chloroimidazo[1,2-a]pyridin-3-yl)sulfonyl]-3-piperidin-4-yl-1,3-dihydro-2H-benzimidazol-2-one;
1-[(1,2-dimethyl-1H-imidazol-4-yl)sulfonyl]-3-piperidin-4-yl-1,3-dihydro-2H-benzimidazol-2-one;
1-[(5-chloro-1,3-dimethyl-1H-pyrazol-4-yl)sulfonyl]-3-piperidin-4-yl-1,3-dihydro-2H-benzimidazol-2-one;
1-[(3,5-dimethylisoxazol-4-yl)sulfonyl]-3-piperidin-4-yl-1,3-dihydro-2H-benzimidazol-2-one;
1-[(2,1,3-benzothiadiazol-4-yl)sulfonyl]-3-piperidin-4-yl-1,3-dihydro-2H-benzimidazol-2-one;
1-(2-naphthylsulfony)-3-(1,2,3,6-tetrahydropyridin-4-yl)-1,3-dihydro-2H-benzimidazol-2-one;
1-[(5-chlorothien-2-yl)sulfonyl]-3-(1,2,3,6-tetrahydropyridin-4-yl)-1,3-dihydro-2H-benzimidazol-2-one;
1-[(5-bromothien-2-yl)sulfonyl]-3-(1,2,3,6-tetrahydropyridin-4-yl)-1,3-dihydro-2H-benzimidazol-2-one;
1-[(4,5-dichlorothien-2-yl)sulfonyl]-3-(1,2,3,6-tetrahydropyridin-4-yl)-1,3-dihydro-2H-benzimidazol-2-one;
1-[(2,5-dichlorothien-3-yl)sulfonyl]-3-(1,2,3,6-tetrahydropyridin-4-yl)-1,3-dihydro-2H-benzimidazol-2-one;
1-[(4,5-dibromothien-2-yl)sulfonyl]-3-(1,2,3,6-tetrahydropyridin-4-yl)-1,3-dihydro-2H-benzimidazol-2-one;
1-[(3-bromo-5-chlorothien-2-yl)sulfonyl]-3-(1,2,3,6-tetrahydropyridin-4-yl)-1,3-dihydro-2H-benzimidazol-2-one;
1-[(4-bromo-5-chlorothien-2-yl)sulfonyl]-3-(1,2,3,6-tetrahydropyridin-4-yl)-1,3-dihydro-2H-benzimidazol-2-one;
1-[(4-bromo-2,5-dichlorothien-3-yl)sulfonyl]-3-(1,2,3,6-tetrahydropyridin-4-yl)-1,3-dihydro-2H-benzimidazol-2-one;
1-[(5-chloro-3-methyl-1-benzothien-2-yl)sulfonyl]-3-(1,2,3,6-tetrahydropyridin-4-yl)-1,3-dihydro-2H-benzimidazol-2-one;
1-[(6-chloroimidazo[2,1-b][1,3]thiazol-5-yl)sulfonyl]-3-(1,2,3,6-tetrahydropyridin-4-yl)-1,3-dihydro-2H-benzimidazol-2-one;
1-[(2,6-dichloroimidazo[2,1-b][1,3]thiazol-5-yl)sulfonyl]-3-(1,2,3,6-tetrahydropyridin-4-yl)-1,3-dihydro-2H-benzimidazol-2-one;
1-[(2-chloroimidazo[1,2-a]pyridin-3-yl)sulfonyl]-3-(1,2,3,6-tetrahydropyridin-4-yl)-1,3-dihydro-2H-benzimidazol-2-one;
1-[(1,2-dimethyl-1H-imidazol-4-yl)sulfonyl]-3-(1,2,3,6-tetrahydropyridin-4-yl)-1,3-dihydro-2H-benzimidazol-2-one;

1-[(5-chloro-1,3-dimethyl-1H-pyrazol-4-yl)sulfonyl]-3-(1,2,3,6-tetrahydropyridin-4-yl)-1,3-dihydro-2H-benzimidazol-2-one;
1-[(3,5-dimethylisoxazol-4-yl)sulfonyl]-3-(1,2,3,6-tetrahydropyridin-4-yl)-1,3-dihydro-2H-benzimidazol-2-one;
1-(2,1,3-benzothiadiazol-4-ylsulfonyl)-3-(1,2,3,6-tetrahydropyridin-4-yl)-1,3-dihydro-2H-benzimidazol-2-one;
a stereoisomer thereof; and
a pharmaceutically acceptable salt thereof.

7. A pharmaceutical composition which comprises a pharmaceutically acceptable carrier and an effective amount of a compound of formula I

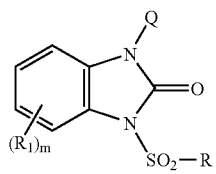
(I)

wherein

Q is 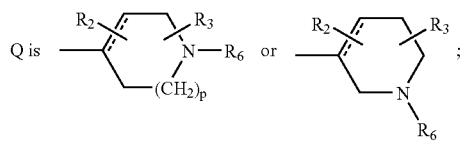

R is an optionally substituted naphthyl, thienyl, benzothienyl, imidazo[2,1-b][1,3]thiazolyl, imidazo[1,2-a]pyridinyl, imidazolyl, pyrazolyl, isoxazolyl, benzothiadiazolyl or pyrindinyl group;
$R_1$ is halogen, CN, $OCO_2R_9$, $CO_2R_{10}$, $CONR_{11}R_{12}$, $SO_xR_{13}$, $NR_{14}R_{15}$, $OR_{16}$, $COR_{17}$ or an optionally substituted $C_1$-$C_6$alkyl group;
m is 0 or an integer of 1, 2 or 3;
$R_2$ and $R_3$ are each independently H or $C_1$-$C_6$alkyl group;
p is an integer of 1;
$R_6$ is H or a $C_1$-$C_6$alkyl;
$R_9$, $R_{10}$, $R_{13}$, $R_{16}$ and $R_{17}$ are each independently H or optionally substituted $C_1$-$C_6$alkyl;
$R_{11}$ and $R_{12}$ are each independently H or an optionally substituted $C_1$-$C_6$alkyl group;
$R_{14}$, and $R_{15}$ are each independently H or an optionally substituted $C_1$-$C_4$alkyl group;
x is 0 or an integer of 1 or 2; and
-----represents a single bond or a double bond; or
a stereoisomer thereof or a pharmaceutically acceptable salt thereof;
wherein the substituent groups which are optionally present are selected from the group consisting of hydrogen, halogen atoms, nitro, cyano, hydroxyl, alkyl, haloalkyl, alkoxy, haloalkoxy, amino, alkylamino, dialkylamino, carboxyl, alkanoyl, alkylthio, alkylsulphonyl, carbamoyl, and alkylaminocarbonyl groups.

8. The composition according to claim 7 having a formula I compound wherein R is an optionally substituted naphthyl, thienyl, benzothienyl or imidazo [2,1-b][1,3] thiazolyl group.

9. The composition according to claim 8 having a formula I compound wherein Q is 4-piperidinyl or 4-(1,2,3,6-tetrahydropyridinyl).

10. The composition according to claim 7 having a formula I compound selected from the group consisting of:
1-[(2-chloroimidazo[2,1-b]pyridin-3-yl)sulfonyl]-3-[2-(dimethylamino)ethyl]-1,3-dihydro-2H-benzimidazol-2-one;
1-(2-naphthylsulfonyl)-3-piperidin-4-yl-1,3-dihydro-2H-benzimidazol-2-one;
1-[(5-chlorothien-2-yl)sulfonyl]-3-piperidin-4-yl-1,3-dihydro-2H-benzimidazol-2-one;
1-[(5-bromothien-2-yl)sulfonyl]-3-piperidin-4-yl-1,3-dihydro-2H-benzimidazol-2-one;
1-[(4,5-dichlorothien-2-yl)sulfonyl]-3-piperidin-4-yl-1,3-dihydro-2H-benzimidazol-2-one;
1-[(2,5-dichlorothien-3-yl)sulfonyl]-3-piperidin-4-yl-1,3-dihydro-2H-benzimidazol-2-one;
1-[(4,5-dibromothien-2-yl)sulfonyl]-3-piperidin-4-yl-1,3-dihydro-2H-benzimidazol-2-one;
1-[(3-bromo-5-chlorothien-2-yl)sulfonyl]-3-piperidin-4-yl-1,3-dihydro-2H-benzimidazol-2-one;
1-[(4-bromo-5-chlorothien-2-yl)sulfonyl]-3-piperidin-4-yl-1,3-dihydro-2H-benzimidazol-2-one;
1-[(4-bromo-2,5-dichlorothien-3-yl)sulfonyl]-3-piperidin-4-yl-1,3-dihydro-2H-benzimidazol-2-one;
1-[(5-chloro-3-methyl-1-benzothien-2-yl)sulfonyl]-3-piperidin-4-yl-1,3-dihydro-2H-benzimidazol-2-one;
1-[(6-chloroimidazo[2,1-b][1,3]thiazol-5-yl)sulfonyl]-3-piperidin-4-yl-1,3-dihydro-2H-benzimidazol-2-one;
1-[(2,6-dichloroimidazo[2,1-b][1,3]thiazol-5-yl)sulfonyl]-3-piperidin-4-yl-1,3-dihydro-2H-benzimidazol-2-one;
1-[(2-chloroimidazo[1,2-a]pyridin-3-yl)sulfonyl]-3-piperidin-4-yl-1,3-dihydro-2H-benzimidazol-2-one;
1-[(1,2-dimethyl-1H-imidazol-4-yl)sulfonyl]-3-piperidin-4-yl-1,3-dihydro-2H-benzimidazol-2-one;
1-[(5-chloro-1,3-dimethyl-1H-pyrazol-4-yl)sulfonyl]-3-piperidin-4-yl-1,3-dihydro-2H-benzimidazol-2-one;
1-[(3,5-dimethylisoxazol-4-yl)sulfonyl]-3-piperidin-4-yl-1,3-dihydro-2H-benzimidazol-2-one;
1-[(2,1,3-benzothiadiazol-4-yl)sulfonyl]-3-piperidin-4-yl-1,3-dihydro-2H-benzimidazol-2-one;
1-(2-naphthylsulfonyl)-3-(1,2,3,6-tetrahydropyridin-4-yl)-1,3-dihydro-2H-benzimidazol-2-one;
1-[(5-chlorothien-2-yl)sulfonyl]-3-(1,2,3,6-tetrahydropyridin-4-yl)-1,3-dihydro-2H-benzimidazol-2-one;
1-[(5-bromothien-2-yl)sulfonyl]-3-(1,2,3,6-tetrahydropyridin-4-yl)-1,3-dihydro-2H-benzimidazol-2-one;
1-[(4,5-dichlorothien-2-yl)sulfonyl]-3-(1,2,3,6-tetrahydropyridin-4-yl)-1,3-dihydro-2H-benzimidazol-2-one;
1-[(2,5-dichlorothien-3-yl)sulfonyl]-3-(1,2,3,6-tetrahydropyridin-4-yl)-1,3-dihydro-2H-benzimidazol-2-one;
1-[(4,5-dibromothien-2-yl)sulfonyl]-3-(1,2,3,6-tetrahydropyridin-4-yl)-1,3-dihydro-2H-benzimidazol-2-one;
1-[(3-bromo-5-chlorothien-2-yl)sulfonyl]-3-(1,2,3,6-tetrahydropyridin-4-yl)-1,3-dihydro-2H-benzimidazol-2-one;
1-[(4-bromo-5-chlorothien-2-yl)sulfonyl]-3-(1,2,3,6-tetrahydropyridin-4-yl)-1,3-dihydro-2H-benzimidazol-2-one;
1-[(4-bromo-2,5-dichlorothien-3-yl)sulfonyl]-3-(1,2,3,6-tetrahydropyridin-4-yl)-1,3-dihydro-2H-benzimidazol-2-one;
1-[(5-chloro-3-methyl-1-benzothien-2-yl)sulfonyl]-3-(1,2,3,6-tetrahydropyridin-4-yl)-1,3-dihydro-2H-benzimidazol-2-one;
1-[(6-chloroimidazo[2,1-b][1,3]thiazol-5-yl)sulfonyl]-3-(1,2,3,6-tetrahydropyridin-4-yl)-1,3-dihydro-2H-benzimidazol-2-one;

1-[(2,6-dichloroimidazol[2,1-b][1,3]thiazol-5-yl)sulfonyl]-3-(1,2,3,6-tetrahydropyridin-4-yl)-1,3-dihydro-2H-benzimidazol-2-one;

1-[(2-chloroimidazo[1,2-a]pyridin-3-yl)sulfonyl]-3-(1,2,3,6-tetrahydropyridin-4-yl)-1,3-dihydro-2H-benzimidazol-2-one;

1-[(1,2-dimethyl-1H-imidazol-4-yl)sulfonyl]-3-(1,2,3,6-tetrahydropyridin-4-yl)-1,3-dihydro-2H-benzimidazol-2-one;

1-[(5-chloro-1,3-dimethyl-1H-pyrazol-4-yl)sulfonyl]-3-(1,2,3,6-tetrahydropyridin-4-yl)-1,3-dihydro-2H-benzimidazol-2-one;

1-[(3,5-dimethylisoxazol-4-yl)sulfonyl]-3-(1,2,3,6-tetrahydropyridin-4-yl)-1,3-dihydro-2H-benzimidazol-2-one;

1-(2,1,3-benzothiadiazol-4-ylsulfonyl)-3-(1,2,3,6-tetrahydropyridin-4-yl)-1,3-dihydro-2H-benzimidazol-2-one;

a stereoisomer thereof; and a pharmaceutically acceptable salt thereof.

11. The compound of claim 1, wherein the substituent groups which are optionally present are selected from the group consisting of hydrogen, halogen atoms, hydroxyl, lower alkyl, lower alkoxy and alkylamino groups.

12. The composition of claim 7, wherein the substituent groups which are optionally present are selected from the group consisting of hydrogen, halogen atoms, hydroxyl, lower alkyl, lower alkoxy and alkylamino groups.

* * * * *